United States Patent [19]

Schroeppel

[11] Patent Number: 4,690,143
[45] Date of Patent: Sep. 1, 1987

[54] PACING LEAD WITH PIEZOELECTRIC POWER GENERATING MEANS

[75] Inventor: Edward A. Schroeppel, Miramar, Fla.

[73] Assignee: Cordis Corporation, Miami, Fla.

[21] Appl. No.: 822,694

[22] Filed: Jan. 24, 1986

Related U.S. Application Data

[63] Continuation of Ser. No. 632,457, Jul. 19, 1984, abandoned.

[51] Int. Cl.$^4$ ............................................. A61N 1/00
[52] U.S. Cl. ........................... 128/419 P; 128/419 PS; 128/419 B; 128/786
[58] Field of Search ...... 128/419 B, 419 PD, 419 PS, 128/675, 784, 786

[56] References Cited

U.S. PATENT DOCUMENTS

| | | | |
|---|---|---|---|
| 2,976,865 | 3/1961 | Shipley | 128/675 |
| 3,421,512 | 1/1969 | Frasier | 128/149 |
| 3,456,134 | 7/1969 | Ko | 310/8.5 |
| 3,563,245 | 2/1971 | McLean | 128/419 |
| 3,657,615 | 5/1972 | Enger | 128/419 P |
| 3,815,611 | 6/1974 | Denniston, III | 128/419 P |
| 3,835,864 | 9/1974 | Rasor et al. | 128/419 P |
| 3,906,960 | 9/1975 | Lehr | 128/419 B |
| 3,943,936 | 3/1976 | Rasor et al. | 128/419 P |
| 4,114,628 | 9/1978 | Rizk | 128/419 PG |
| 4,140,132 | 2/1979 | Dahl | 128/419 PG |
| 4,316,472 | 2/1982 | Mirowski et al. | 128/419 D |
| 4,432,363 | 2/1984 | Kakegawa | 128/419 PS |

OTHER PUBLICATIONS

Myers et al., "IEEE Transactions on Biomedical Engineering", vol. 10, No. 2, Apr. 1963, p. 83.
Sussner, "1979 IEEE Ultrasonics Symposium", 1979, pp. 491–498.
Hunklinger, et al., New Dynamic Aspects of Amorphous Dielectric Solids, from Festkorperprobleme XVI, (1976).
Sussner, et al., "Colloid and Polymer Science", vol. 275, 1979, pp. 591–602.
Hausler, et al., Piezoelectric High Polymer Foils as Physiological Mechanic–Electric Energy Converters, IEEE 1980 Biomedical Group Annual Conference, Frontiers of Engineering in Health Care.
Marcus, M. A., Ferroelectric Polymers and their Applications, Ferroelectrics, vol. 40, 1982.

*Primary Examiner*—William E. Kamm
*Attorney, Agent, or Firm*—Henry W. Collins; Thomas R. Vigil

[57] ABSTRACT

The pacing lead includes a catheter distal end portion which has a piezoelectric device therein and which is adapted to be inserted into a human heart. The device can be a ceramic bimorph or can be made of polyvinylidene fluoride film for generation of electrical energy upon contraction of the heart. The piezoelectric device is designed to generate electrical energy in response to movement of the implanted pacing lead and in the preferred embodiment is incorporated into the wall of the catheter of the lead as a longitudinal or spiral configured strip of film having piezoelectric properties.

7 Claims, 3 Drawing Figures

PACING LEAD WITH PIEZOELECTRIC POWER GENERATING MEANS

This is a continuation of application Ser. No. 632,457 filed July 19, 1984, now abandoned.

BACKGROUND OF THE INVENTION

1. Field of the Invention

The present invention relates to a self-contained power source mounted in a pacing lead for generating electrical power for operating a pacing lead. The pacing lead is of the type designed to be implanted in a living organism, such as within a human's heart, such that movement of the heart acting on the pacing lead will cause generation of electrical power.

2. Description of the Prior Art

Heretofore various methods have been employed for generating electrical energy for electronic implants. In the Ko U.S. Pat. No. 3,456,134 there is disclosed an encapsulated cantilevered beam composed of a piezoelectric crystal mounted in a metal, glass or plastic container and arranged such that the cantilevered beam will swing in response to movement. The cantilevered beam is further designed to resonate at a suitable frequency and thereby generate electrical voltage.

In the Dahl U.S. Pat. No. 4,140,132 there is disclosed a piezoelectric crystal mounted in cantilevered fashion within an artificial pacemaker can or case, having a weight on one end, and arranged to vibrate to generate pulses which are a function of physical activity.

In the McLean U.S. Pat. No. 3,563,245 there is disclosed a pressure actuated electrical energy generating unit. A pressurized gas containing bulb is inserted into the heart whereby the contractions of the heart exert pressure on the bulb and cause the pressure within the bulb to operate a bellows remotely positioned with respect to the heart. This bellows in turn operates an electrical-mechanical transducer.

Further it has been proposed in the Frasier U.S. Pat. No. 3,421,512 to provide a pacer with a biological power supply which generates electrical power for the pacer utilizing a body fluid as an electrolyte.

It has also been suggested in the Enger U.S. Pat. No. 3,659,615 to use a piezoelectric bimorph encapsulated and implanted adjacent to the left ventricle of the heart and arranged to flex in reaction to muscular movement to generate electrical power.

Heretofore mounting of an power generation device in a catheter or tubing has not been proposed. However, the mounting of a sensor in a catheter has been proposed. For example, in the Shipley U.S. Pat. No. 2,967,865, strain gauges are used in a spiral configuration around a catheter to sense and transmit information regarding heart contractions.

Also, the use of piezoelectric material in the form of foils or bands wrapped around a patient's chest or leg has been experimentally suggested for measuring heart beats and blood flow. See for example "Ferroelectric Polymers and their Application" by Michael A. Marcus, appearing in "Ferroelectrics": 40 1982, and "Piezoelectric High Polymer Foils as Physiological Mechanic-Electric Energy Converters" by E. Hausler, H. Lang and F. J. Schreiner, appearing in "IEEE 1980 Biomedical Group Annual Conference, Frontiers of Engineering in Health Care".

SUMMARY OF THE INVENTION

According to the teachings of the present invention a piezoelectric power generation device is mounted in a pacing lead comprising a catheter which is inserted pervenously into a human heart. The device comprises piezoelectric material such as a bimorph, multimorph, or piezoelectric film arranged within the catheter to flex therewith in response to motion of the heart contractions for continuous generation of electrical power.

DESCRIPTION OF THE PREFERRED EMBODIMENTS

Figure 1:
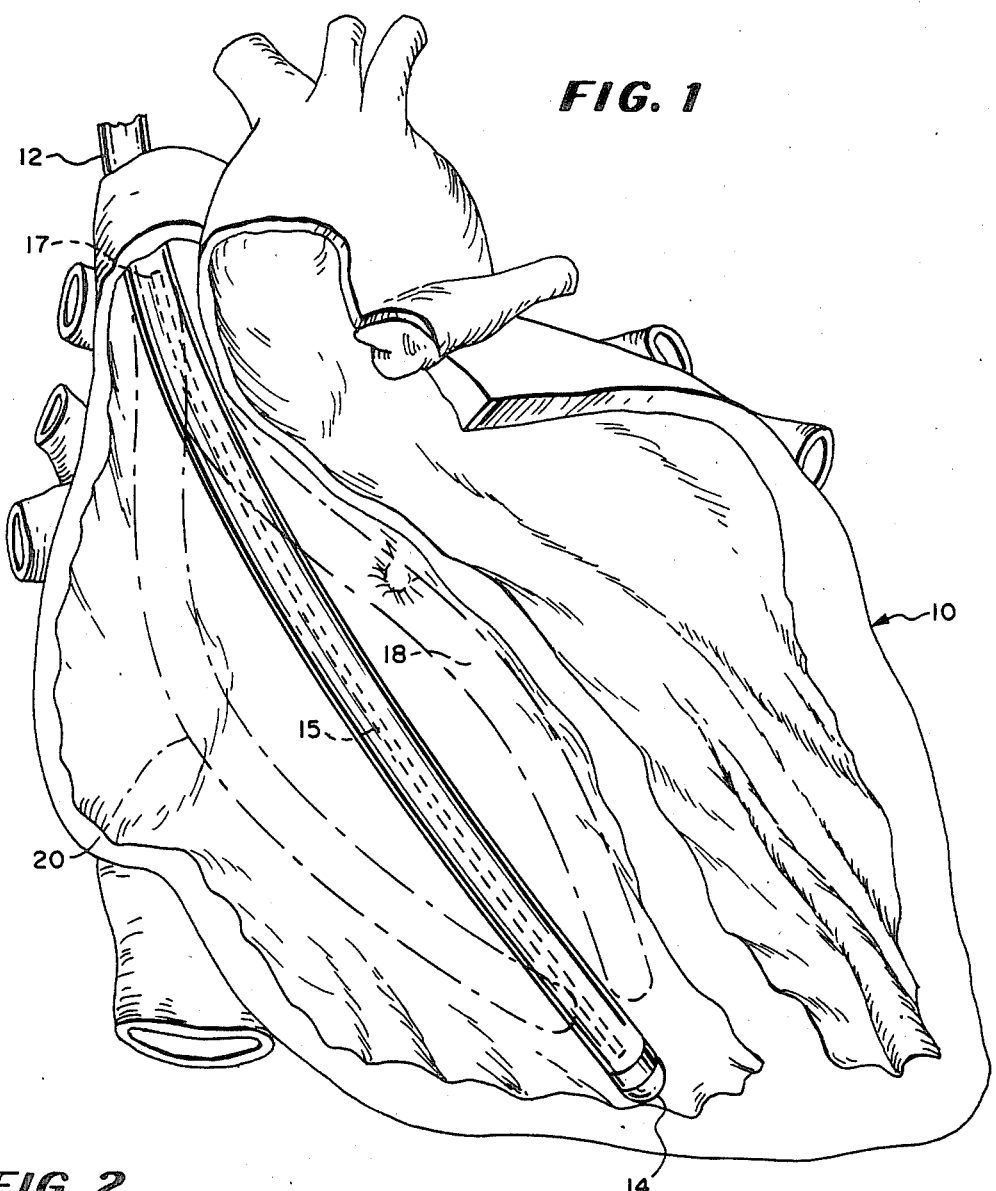
FIG. 1 is a perspective view of a heart with portions broken away and shows one embodiment of the pacing lead of the present invention inserted within a human heart and employing a piezoelectric generator comprising a piezoelectric film strip embedded in the lead body.

Turning now to FIG. 1, there is illustrated therein a partially cut-away pictorial view of a human heart 10. A catheter body 12 is shown protruding into a heart chamber. Typically the catheter body 12 is part of a unipolar or bipolar pacing lead having electrodes therein such as tip electrode 14 for providing pacing stimulus to the heart. Conventionally, the pacing tip electrode 14 is connected by coiled wire conductors (not shown) enclosed within the hollow center or lumen of the catheter body 12 to a proximal terminal electrode (not shown). The coiled wire conductor extends from the distal end to the proximal end of the pacing lead where it is adapted to be coupled to conventional pacer circuitry.

According to the teachings of the present invention, an electrical power generating device 15 is shown in FIG. 1 positioned within the lead or catheter body 12. Such device 15 comprises a multilayered strip of thin piezoelectric film polymer such as polyvinylidene fluoride ($PFV_2$). This multilayered film strip 15 extends in the lead body 12 or wall thereof from a point near the distal tip electrode 14 to a proximal end 17 thereof near where the catheter/lead body 12 exits from the heart 10. The strip 15 is arranged to be electrically isolated from the external environment and also from any internal conductors which may be placed within the lumen of the catheter/lead body 12.

During movement of the heart muscle during contraction thereof the catheter/lead body 12 is caused to bend, which bending is graphically illustrated in FIG. 1 by phantom lines 18 and 20. This flexing of the piezoelectric film 15 generates electrical power in a process well known in the art and such power may be tapped by the attachment of appropriate conductors to the piezoelectric film 15, which conductors would extend from the proximal end 17 of the film strip 15 to the proximal end of the catheter/lead body 12 for electrical connection to circuitry for filtering and storing the generated electrical power. An example of such circuitry is shown in FIG. 1 of and drawings in the Ko U.S. Pat. No. 3,456,134 directed to a piezoelectric energy converter for electronic implant. FIG. 1 and the accompanying description of FIG. 1 in this patent is incorporated herein by reference.

Figure 2:
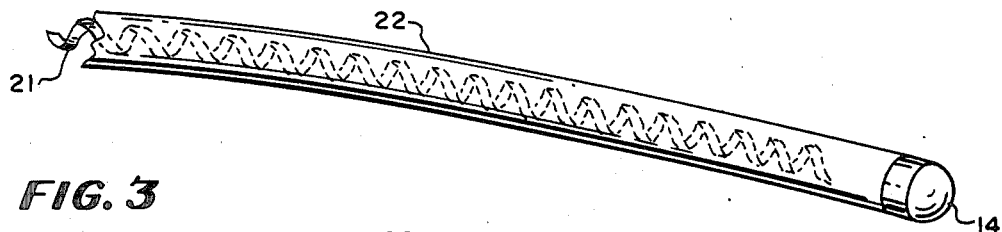
FIG. 2 is a fragmentary perspective view of an alternate embodiment of the piezoelectric generator which comprises a spiral arrangement of a piezoelectric film strip.
Figure 3:
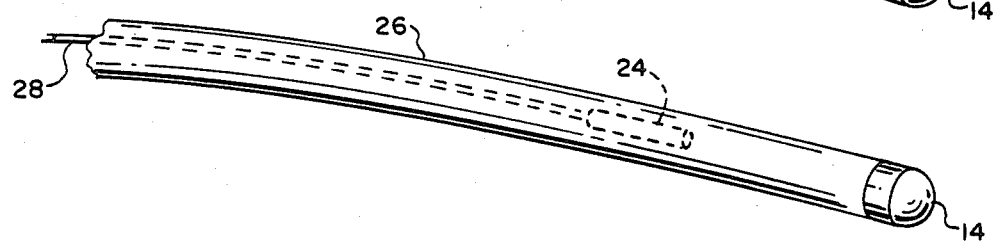
FIG. 3 is a fragmentary perspective view of a third alternate embodiment of the piezoelectric generator which comprises a bimorph.

In another embodiment of the present invention, there is provided (FIG. 2) a spiral coil 21 of multilayered piezoelectric film, having the same composition as the above described film 15, arranged within a catheter/lead body 22. In this spiral coil arrangement, a larger quantity and length of film 21 may be used to thereby boost the electrical power generated thereby. This spiral coil or strip 21 is similarly arranged to be electrically isolated from the external environment and also from any internal conductors which may be placed within the lumen of the catheter/lead body 12. As before, flexing of the catheter strains the piezoelectric film to generate electrical energy.

In still a further embodiment of the present invention, there is provided a ceramic piezoelectric bimorph 24 arranged within a catheter 26 to flex therewith and thereby generate electrical power. Conductors 28 connected to the bimorph 24 are shown extending from the proximal end of the bimorph 24 through the catheter/lead body 26. The bimorph 24 is generally comprised of a pair of sheets of piezoelectric material, such as barium titanate, lead titanate zirconate, lead metaniobate and/or sodium bismuth titanate. Conventionally the piezoelectric sheets are separated by a shim of material such as brass. A bimorph of this type is generally available and can be obtained from Piezoelectric Products, Inc., or from Vernitron Piezoelectric Division.

While various embodiments of the power generation device of the present invention have been described above, it is to be understood that variations and modifications and equivalent structure can be made without departing from the teachings of the present invention. Accordingly, the scope of the invention is only to be limited as necessitated by the accompanying claims.

I claim:

1. A pacing lead comprising a lead body having a distal end portion and a distal end, said lead body comprising a catheter having a given wall thickness and an interior lumen, a tip electrode mounted at the distal end of said lead body for providing electrical stimulus to a heart wall, a wire conductor in said catheter lumen extending the length of said catheter, being connected at one end to said tip electrode and being connectable at the other end to a pacer, piezoelectric electrical power generating means associated with said lead body distal end portion for generating electrical power in response to flexing movement of said pacing lead during contractions of the heart, within the heart and without any electrical power being supplied to said piezoelectric electrical power generating means, and electrical conducting means in said catheter coupled to said piezolectric electrical power generating means and adapted to be coupled to a pacer for providing electrical power to the pacer.

2. The pacing lead of claim 1 wherein said piezoelectric generating means comprise polyvinylidene fluoride film.

3. The pacing lead of claim 2 wherein said piezoelectric generating means further comprise a multilayered strip of said polyvinylidene fluoride film longitudinally disposed within said catheter distal end portion.

4. The pacing lead of claim 3 wherein said film strip is mounted in the wall of the catheter.

5. The pacing lead of claim 2 wherein said piezoelectric generating means further comprise a multilayered strip of polyvinylidene fluoride film arranged in a spiral configuration within said catheter distal end portion.

6. The pacing lead of claim 5 wherein said spiral film strip is mounted within the wall of said catheter.

7. The pacing lead of claim 1 wherein said piezoelectric generating means comprise a ceramic piezoelectric bimorph arranged within said catheter distal end portion.

* * * * *